United States Patent [19]

Brinton

[11] 4,454,116

[45] * Jun. 12, 1984

[54] **IMMUNIZATION OF HUMANS AGAINST ENTEROTOXOGENIC INFECTION BY *ESCHERICHIA COLI***

[75] Inventor: Charles C. Brinton, Pittsburgh, Pa.

[73] Assignee: Bactex, Inc., Pittsburgh, Pa.

[*] Notice: The portion of the term of this patent subsequent to Dec. 2, 1997 has been disclaimed.

[21] Appl. No.: 187,051

[22] Filed: Sep. 15, 1980

Related U.S. Application Data

[63] Continuation-in-part of Ser. No. 854,343, Nov. 23, 1977, Pat. No. 4,237,115.

[51] Int. Cl.³ .................... A61K 39/108; A61K 39/00
[52] U.S. Cl. ........................................ 424/92; 424/88
[58] Field of Search ................... 424/8, 12, 85, 87, 88, 424/92; 436/547

[56] References Cited

U.S. PATENT DOCUMENTS 4,237,115  12/1980  Brinton .................................. 424/92

FOREIGN PATENT DOCUMENTS 2617870  12/1976  Fed. Rep. of Germany .
1549345   8/1979  United Kingdom .

OTHER PUBLICATIONS

Morgan, Inf. & Immunity, vol. 22, 1978, pp. 771–777.
Brinton, Nature, vol. 183, Mar. 21, 1959, pp. 782–786.
Brinton et al., Biochim. Biophys. Acta., vol. 42, 1960, pp. 298–311.
Brinton, Trans. NY Acd. Sci., Ser. II, vol. 27, Jun. 1965, pp. 1003–1053.
Brinton, Trans. NY Acd. Sci., vol. 27, 1965, pp. 1003–1054.

*Primary Examiner*—Blondel Hazel
*Attorney, Agent, or Firm*—Omri M. Behr

[57] ABSTRACT

There is provided a vaccine material capable of providing substantial levels of protection against human disease caused by infection with *Escherichia coli*. The protecting means comprises pili of the infecting organism. The protection is given either by administering the pili directly to the subject to be protected or to a pregnant or lactating female where protection of the newborn is desired.

4 Claims, No Drawings

IMMUNIZATION OF HUMANS AGAINST ENTEROTOXOGENIC INFECTION BY *ESCHERICHIA COLI*

RELATED APPLICATIONS

This application is a continuation-in-part of applicants copending application Ser. No. 854,343 filed Nov. 23, 1977, now U.S. Pat. No. 4,237,115 issued Dec. 2, 1980.

BACKGROUND OF THE INVENTION

*Escherichia coli* is a ubiquitous pathogen of man and animals causing a wide variety of diseases of clinical and economic importance. The greatest cause of mortality in the world is infant death and *E. coli* diarrheal disease in areas of poor sanitation is one of the most important causes. *E. coli* has been estimated to cause about 40% of all travelers diarrhea. *E. coli* is the most frequent cause of hospital-acquired infections and infections of debilitated and traumatized persons. Bacteremias and burn-wound infections are frequently due to *E. coli. E. coli* is the most frequent cause of urinary tract infections causing acute and chronic cystitis and pyelonephritis. It is clear that the development of methods to prevent *E. coli* disease would alleviate much human misery and stop huge economic losses.

Applicant has surveyed a large number of pathogenic strains of *E. coli* from a number of human diseases and established that the great majority of them possess pili belonging to a single immunologically related family named "*E. coli* Type 1" pili. In a co-pending application (BTX 3.0-005) U.S. Ser. No. 187,049 filed Sept. 15, 1980 which is incorporated herewith by reference, there is disclosed a general methodology of serological analysis. This methodology shows that members of the *E. coli* Type 1 pilus family can be ranked in a hierarchial order from most senior to most junior. Antisera to the most senior pilus type can cross-react to a large extent with all other members in the family. Therefore, provision of a vaccine consisting of a single type of purified *E. coli* Type 1 pili would protect against the great majority of *E. coli* infections of humans, that is, infections caused by strains bearing pili in the Type 1 family especially those strains with pili junior to the pili in the vaccine. There also exist other immunologically related families of pili on *Escherichia coli* strains pathogenic for humans. These families are unrelated immunologically to Type 1 pili associated with mannose-sensitive hemagglutination of guinea pig erythocytes. These are known as NSM pili. Vaccines derived from NMS pili would also be useful in providing protection against the various *E. coli* infections.

SUMMARY OF THE INVENTION

There are provided vaccine compositions capable of raising the antibody level of a human subject to a level sufficient to provide protection against infection caused by organisms of a first group of strains of piliated *E. coli* comprising:

(a) Pili derived from a second group of strains of piliated *E. coli* organisms wherein cells of organisms of said first group are cross-reactive with serum containing antibodies against pili from said second group, said first group consisting of strains which may be the same or different from, and suitably junior to, the strains of said second group; and, (b) a pharmaceutically acceptable carrier.

There is exemplified in this application a vaccine containing pili from a single predetermined strain which is effective against infection caused by organisms of the same strain. Vaccines which contain both Type 1 and NMS pili are also included within the scope of the present invention provided, of course, that of said pili will cross-react immunologically with at least one of the infecting organisms.

An important enterotoxogenic strain of *E. coli* was isolated from humans with diarrhea and shown to be virulent and causative of the natural disease when inoculated into non-immune humans. This virulent strain, though sparsely piliated, was grown and selected for well-piliated clones. These clones were grown and maintained on minimum glucose base agar medium and the pili therefrom separated from the cells and subjected to several cycles of crystallization in aqueous magnesium chloride followed by resolubilization in low ionic strength neutral buffer.

Test subjects were injected with pili. Thereafter, the subjects were challenged intragastrically with an amount of *E. coli* previously found to cause infection in non-immune subjects.

Although incidence of diarrhea was noted in the immunized group, members of this group recovered rapidly relative to the non-immunized challenge group.

Culture of *E. coli* H 10407

Samples of a parental strain *E. coli* H 10407 (078:H11) was isolated from a patient suffering from severe diarrhea in Bangladesh. The sample was passed through still broth, and colonial forms selected therefrom to provide a well piliated clone designated *E. coli* H 10407 (ATCC 31703). The clone is then grown on minimal glucose agar base medium. The pili were separated from the cells by blending and centrifugation in a low ionic strength neutral buffer such as phosphate buffer and saline pH 7.0. The pili are crystallized from the buffer by addition thereto of concentrated magnesium chloride (aq) to bring the strength of the buffer up to the 0.10 M whereupon the pili crystallize. The crystalline pili are taken up in a low ionic strength neutral buffer such as 0.04 M phosphate buffer pH 7.0 (without saline) and reprecipitated with magnesium chloride in a similar manner. It is preferred to subject the pili to from one to five cycles of crystallization. The procedure used is that substantially set forth in Brinton, *Trans. N.Y. Acad. Sci* 27, 1003 (1965).

The final preparation of the pilus vaccine consists of blending and filtering the recrystallized pili through sterile filters suitably with a preservative such as merthiolate. The pili thus prepared are of a quality sufficient to pass the standards of the Burean of Biologics, Food and Drug Administration for general safety, sterility, and pyrogenicity.

The pili may be administered orally—say, in capsule form—or by injection—that is to say, subcutaneous, intradermal, or intramuscular injections. Where the mode of administration is by injection, since the pili are solid, any pharmaceutically acceptable suspending medium may be employed. It has been found especially useful to employ phosphate buffer, suitably containing merthiolate, as the vehicle or suspending medium. It is preferred to use 0.005–0.1, most suitably 0.04, ionic strength phosphate buffer containing 0.005 to 0.1, most suitably 0.01%, merthiolate. The concentration of NMS pili (associated with non-mannose-sensitive hemagglutination of human erythocytes in the vehicle is not critical. The sole criterion of desirability being that the pili shall be sufficiently finely divided to provide a suspension which meets generally accepted standards of syringeability. A concentration of 1–30, preferably about 20 mg of pilus protein per 10 ml of suspending medium is especially suitable.

It is generally preferred to administer the vaccine composition in more than one dose separated by a predetermined time factor. This time factor is selected to permit the formation of an adequate titer of antibodies to the pili in the injected subject. It has been found suitable to administer the vaccine composition at least once, preferably at 60 and again at 30 days pre-infection.

Since there are no local or systemic toxic effects engendered by the injection of vaccine, there appear to be no upper limits to the dosage administered. It has been found suitable, however, to administer between 1 and 100 micrograms of pili per kilogram of body weight, most suitably about 20 milograms per kilogram of body weight per injection.

E. coli infection occurs, due to many different strains thereof, in different species of mammals. It has been found that E. coli species having Type 1 pili are responsible for human infections. Thus, the pili derived from related members of said group of species will provide protecting antibodies in a system into which they are administered.

EXAMPLE I

Preparation of Escherichia Coli Pili (Type)

A culture prepared by resuspending piliated phase colonies growing on minimal glucose agar base medium in a liquid 2 broth (1% Bactotryptone, 0.8% NaCl, 0.1% yeast extract, 0.1% glucose) medium was used to inoculate trays containing the same growth medium solidified with agar. After overnight incubation at 37° C., the confluent bacterial growth was suspended in 0.01 molar phosphate buffered saline pH 7.0. About twenty milliliters of buffer was used to suspend the growth from one tray which dimensions were approximately 30 cm×40 cm. The resuspended growth was blended, 200 milliliters at a time, at 14,000 rpm for five minutes in the 400 milliliter cup of a Sorvall OMNIMIXER in order to remove pili from the cells. Cells were then removed by centrifugation at 10,000 times G for twenty minutes and the supernatant liquid was retained. The pili were then crystallized by the addition of magnesium chloride ($MgCl_2$) to 0.1 molar. After the crystals formed, they were removed from suspension by centrifugation at 20,000 times G for sixty minutes, and the pellet was retained. The pellet containing the pilus crystals was redissolved in 0.04 phosphate molar buffer pH 7.02 (without saline). The suspension was clarified by centrifugation at 20,000 times G for sixty minutes and the supernatant liquid was retained. The cycle of crystallization, centrifugation, redissolution, and centrifugation was repeated two to four times to obtain the purified pilus suspension.

EXAMPLE II

Vaccine Preparation (a) High speed blending with Sorvall Omnimix at 14,000 rpm for 10 minutes with 100 ml aliquots in a 200 ml cup, broke up pilus aggregates and shears the rods 0.01% merthiolate added and (b) Concentration was determined by U.V and adjusted to a 1800 mcg/10 ml dosage form.

Removal of Flagella

Cycled solubilized pili preparation were adjusted to pH 12–3 by addition of 1 N sodium hydroxide, after 30 minutes, at room temperature with occasional stirring, the pili were precipitated by addition of 10% (u/v) saturated ammonium sulphate followed by centrifugation at 20,000 G for 30 minutes leaving dissociated flagella subunits in the supernate.

The precipitated pili were then resolubilized in phosphate buffer (0.04 M).

EXAMPLE III

Immunization

Sequential groups of 3–6 volunteers (21 in total) were parenterally inoculated in the triceps muscle with 45, 90, 90 or 1800 mcg doses of purified pili vaccine. Twenty-eight days thereafter 15 of the 21 volunteers received a booster IM inoculation with 1800 mcg of pili vaccine. Volunteers who received 1800 mcg primary or booster inoculations were also given an order to assess local reactions due to pili rather than the act of IM innoculation per se. Neither the volunteer nor the examining physician was told which ar received vaccine and which received saline.

Challenge Study

Approximately one month following inoculation with the 18 mcg booster dose (two months after primary immunization), six vaccines and seven unimmunized control volunteers participated in a challenge study to assess vaccine efficacy.

EXAMPLE IV

Preparation of Inocula

The E. coli H 10407 parent strain utilized in previous challenge studies was inoculated into Z broth, incubated for 4 hours with shaking at 30° C. and frozen at −70° C. with DMSO. The frozen stock was later thawed and streaked onto casamino-yeast extract (CAYE) agar plates.

Inocula and Challenge

After 15 hours incubation at 30° C. 16 piliated colonies identified under stereo-microscope were picked and streaked on CAYE agar. Twelve hours after incubation at 37° C., 30 piliated colonies were used to heaving inoculate each of six CAYE agar plates for incubation at 37° C. After twelve hours, the CAYE agar cultures were harvested with saline (0.85%) and dilutions made in saline.

EXAMPLE V

Administration of Inoculum

Two gm of $NaHCO_3$ were dissolved in 150 ml of distilled water of which the volunteers drank 120 ml; one minute later they drank the remaining 30 ml in which the E. coli inoculum ($5 \times 10^8$ organisms) was suspended. Inoculum size was quantitated by replicate pour-plate technique before and after challenge. The presence of both type 1 somatic and NMS piliation on the challenge organisms was documented by agglutination with specific antisera.

Clinical Observations

Immunization

Volunteers were kept under close observation on the Isolation Ward for two days post-inoculation with pili vaccine. Oral temperatures were taken every six hours and injection sites were examined for erythema, heat, induration and tenderness.

Challenge

Volunteers were examined daily starting three days prior to ingesting the virulent organisms. Oral temperatures were taken every six hours and repeated within five minutes if they were 37° C. or above. All stools and vomitus were collected in plastic cholera seats, examined by a nurse or physician and volumes measured. Stools were graded on a five point scale—grades 1 (fully formed) and 2 (soft) were considered normal; grade 3 denoted thick liquid stool, grade 4 opaque-watery, and grade 5 rice-water stools. Diarrhea was defined as three or more loose (grade 3–5) stools in 24 hours or at least two loose stools within 24 hours surpassing 250 ml in volume. Prior to discharge all volunteers received a five-day course of oral neomycin (500 mg six hourly) to eradicate fecal carriage of the virulent ETEC strain.

received primary inoculations with 45 (2), 900 (2) and 1800 (2) mcg doses of vaccine. Local reactions were evident 24 hours post-inoculation but, with one exception, were gone by 48 hours. The reactions were described as mild to moderate by the volunteers. In no instance did nausea, vomiting, diarrhea or fever occur.

Vaccine Efficacy

Clinical:

One month after IM inoculation with an 1800 mcg booster dose of pili vaccine, six vaccinees agreed to participate in a challenge study along with seven unimmunized control volunteers. Following ingestion of $5 \times 10^8$ virulent *E. coli* H 10407 bacteria all seven controls developed diarrheal illness (Table 5). Three controls passed copious rice-water stools resulting in cholera-like total diarrheal stool volumes of 3.8, 7.5 and 9.9 liters; two controls required intravenous fluids to maintain hydration. In contrast, only 2 of 6 vaccinees developed diarrheal illness (p=0.04, Fisher's Exact Test). While ill controls experienced malaise (7 of 7) and vomiting (6 of 7), none of the vaccinees, ill or well, had these complaints (Table 5). Otherwise, the diarrheal illness manifested by the two vaccinees was similar in incubation, total volume number of loose stools and duration to that seen in the controls.

TABLE 1

RESPONSE OF VACCINEES IMMUNIZED WITH TWO PARENTERAL DOSES OF PURIFIED *E. COLI* TYPE 1 SOMATIC PILI VACCINE AND CONTROLS FOLLOWING INGESTION OF $5 \times 10^8$ VIRULENT ENTEROTOXIGENIC *E. COLI* (STRAIN H10407)

|  | Mean Incubation (hrs) | Diarrhea | Mean Total Diarrheal Stool Volume per Ill Volunteer | Mean Total No. Loose Stools per Ill Volunteer | Vomiting | Malaise | Fever | Positive Stool Culture |
|---|---|---|---|---|---|---|---|---|
| Vaccinees | 36.5 | 2/6* p=0.04 | 3.89+ (1.38–6.40)** | 16 (15–19)** | 0/6 | 0/6 | 0/6 | 6/6 |
| Controls | 34.5 | 7/7 | 3.96 (1.37–9.86) | 18 (7–29) | 6/7 | 7/7 | 2/7 | 7/7 |

*No. positive/No. challenged
+liters
**(range)

TABLE 2

CLINICAL RESPONSE OF VOLUNTEERS TO PARENTERAL IMMUNIZATION WITH PURIFIED H10407 TYPE 1 SOMATIC PILI VACCINE

|  | Following Initial Vaccine Dose | | | Following 1800 mcg. Booster Dose | | |
|---|---|---|---|---|---|---|
| Dose | Fever | Malaise | Local Reactions | Fever | Malaise | Local Reactions |
| 45 mcgs. | 0/3* | 0/3 | 0/3 | 0/3 | 0/3 | 2/3 |
| 90 mcgs. | 0/4 | 0/4 | 0/4 | 0/3 | 0/3 | 0/3 |
| 900 mcgs. | 0/4 | 0/4 | 0/4 | 0/3 | 0/3 | 2/3 |
| 1800 mcgs. | 0/10 | 0/10 | 0/10 | 0/6 | 0/6 | 2/6 |

*No. with reactions/No. immunized

RESULTS

Reactogenicity

Clinical:

Neither erythema, induration, heat, tenderness, fever nor malaise occurred in any of the 21 volunteers who received primary immunization with varying dose of purified pili vaccine (Table 1). Among the fifteen persons who received an 1800 mcg booster inoculation no systemic adverse reactions were noted but six vaccinees developed objective local adverse reactions including induration, heat or erythema (Table 2). Local reaction following the booster occurred in persons who had

EXAMPLE VII

In my co-pending application filed contemporaneously herewith (BTX 3.0-005) U.S. Ser. No. 187,049, there is disclosed the concept of hierarchy of strains within a group of immunologically related piliated organisms. In said application I show how the senior organisms of the group may be identified and said senior organisms protect against infection by junior organisms. The disclosure of said application is incorporated herein by reference.

Hence with respect to *E. coli* vaccines, compositions derived from senior strains will protect against infections by junior strains.

In Table 3 below there is shown a normalized cross-reactivity table under the principles of my co-pending application therefore vaccines produced as shown from E25 (ATCC 31703) pili will protect against infection by strains junior thereto including H 10407 (ATCC 31705).

While these principles are disclosed with respect to type 1 pili, they are equally applicable to the NMS pili, vaccines derived from which are expressly included within the scope of the present invention.

TABLE 3

TABLE OF SENIOR/JUNIOR HIERARCHY
*E. COLI* TYPE 1 PILUS FAMILY

| Pili | Antisera | | | | |
|---|---|---|---|---|---|
| | E25 | B9 | H10407 | TD | E28 |
| E25 | 100 | 62 | 8 | 10 | 2 |
| B9 | 142 | 100 | 9 | 14 | 2 |
| H10407 | 16 | 25 | 100 | 8 | 14 |
| TD | 48 | 57 | 31 | 100 | 12 |
| E28 | 34 | 41 | 51 | 19 | 100 |

EXAMPLE VIII (a) Isolation and characterization of piliated phase *E. coli* (NMS Pili)

The original H 10407 parent culture was passed on casamino acid-yeast extract (CAYE) agar (Appendix), and resulting colonies were screened for hemagglutination of human red blood cells that was not sensitive to inhibition with D-mannose (NMS=non-mannose sensitive). When such a clone was detected, it was passed continuously on CAYE agar. Piliation was verified by electron microscopic examination and was observed to be morphologically distinguishable from Type 1 piliated clones of H 10407 isolated from the same parent. NMS pili are rods 50–60 A in diameter like Type 1 pili, but they are more flexible and unwind to form thin fibers (10–20 A diameter).

The NMS colony type is smaller and lighter in pigmentation than the Type 1 piliated or nonpiliated colony types when grown under these conditions. When NMS clones are passed continuously on CAYE plates there are very few reversions detectable after 10–14 hours at 37° C.

H 10407 can produce two different kinds of hemagglutinins. One kind, Type 1 pili, participates in a mannose-sensitive hemagglutination with guinea pig and human red blood cells and has been shown to be Type 1 pili. The other kind of hemagglutin is responsible for a non-mannose-sensitive hemagglutination with human red blood cells but not guinea pig cells. Clones possessing the latter factor are referred to as NMSP+.

(b) Growth

Because the subtle differences in NMS colonial morphology could best be detected in 10–14 hour cultures, clones were maintained by continuous subculture every 12 hours on CAYE agar. Five to six colonies were picked to avoid selecting atypical mutants. Furthermore, growth in liquid media severely depleted the cultures of NMS-piliated cells. Therefore, cultures for the inoculation of large growth trays (10½×15½×1 inch) had to be prepared on solid media both using CAYE agar. Growth for inoculation was harvested off CAYE agar in petri dishes using 7.5 ml of 0.7% casamino acids for dish and scraping the agar surface with a bent glass rod. The suspended growth was then pipetted out of the dish and used to inoculate 2 large growth trays, 2–3 ml per tray. After inoculation, the trays were covered with tightly fitted aluminum lids and incubated for 19–21 hours at 37° and 70% relative humidity in a dedicated floor model humidified incubator located in the adjacent room.

After incubation, the growth trays were returned to the vaccine facility for harvesting. Trays were inspected visually for contamination. Cultures were harvested with the addition of 5–8 ml harvest buffer using a clean glass plate to scrape the growth off the agar surface. Suspended growth was aspirated into a sterile flask and kept on ice until the entire day's harvest was collected. The polled harvest was then treated as described in the following section.

(c) Isolation of NMS pili

To remove pili from the cells, the harvest suspension was blended in 200 ml portions in an ice chilled cup using the Sorvall Omnimixer. Each portion was blended for 5' at 11,700–13,000 rpm, as determined by 3 to 4 readings with a tachometer. Approximately half of an 80 tray harvest was blended and centrifuged before blending the remaining half. The blended harvest was centrifuged at 15,380 g for 25 minutes to remove the cells. The cell pellets were discarded.

Supernatants of blended cultures were pooled and the volume measured. Crystalline ammonium sulfate was added slowly to 20% saturation with constant stirring. (In contrast to Type 1 pili, NMS pili could not be crystallized by $Mg++$.) Streaming birefringence was immediately visible. The preparation was allowed to crystallize overnight in the cold. NMS pilus crystals were pelleted at 30,050 g for 60 minutes, and the supernatant discarded. The pellets of crystalline pili were then solubilized by magnetic stirring for about 1 hour, followed by standing in the cold overnight in solubilizing buffer. One liter of solubilizing buffer was used per 80-tray harvest batch. The solubilized preparation was clarified by centrifugation at 30,000 g for 60 minutes.

The cycle of crystallization/solubilization was repeated for a second time by measuring the exact volume of the clarified supernatant and adding crystalline ammonium sulfate to 20% saturation, slowly and with stiring. The preparation was allowed to sand in the cold overnight, then centrifuged at 30,050 g to pellet the pilus crystals. The same sequence as before was repeated for solubilization and clarification.

The third cycle of purification was the same as the second, except that only 500 ml of buffer were used to solubilize the crystals. All preparations were monitored by darkfield microscopy and SDS-PAGE throughout the purification procedure.

Pilus preparations were allowed to equlibrate to room temperature for about 20 minutes. The pH was then adjusted to 2.5 using 0.2 N HCl, with rapid stirring. The pH-adjusted solutions were allowed to stand at room temperature for 5–8 minutes, then immediatel centrifuged at 30,050 g for 60 minutes. Pilus-containing supernatants were decanted and immediately readjusted to pH 7.0–7.2 with 0,2 N NaOH. The brownish flagellar material in the pellet was discarded. Crystalline ammonium sulfate was added to the supernatant to 20% saturation and crystallization was allowed to continue overnight in the cold. At this point, preparations at identical stages of purification were pooled, forming 2 pools of NMS pili for ease in handling. The flagella removal procedure was repeated on these 2 pools until the amount of flagella was reduced to less than 1%, as measured by SDS-PAGE.

EXAMPLE IIX

Vaccine Preparation

The preparation was dilated to 0.5 mg/m/ and prefiltered once through a 45μ Gelman filter using a 142 mm Millipore disc filtration unit with a 2 liter capacity cylinder. Merthiolate is added to a final concentration of 0.01% and the final vaccine material was then filter sterilized in a single filling under positive pressure through the sterilized unit and collected in a sterile receiving bottle.

Pilus vaccines have been shown to be optimally antigenic in rabbits at doses of about 1 μg/kg body weight. For the average adult male of body weight 150 lbs, this requires injection of about 1.0 ml of vaccine at a concentration of 0.5 mg/ml.

TABLE 3

ELISA Titers of Sera from NMS Immunized and Nonimmunized Humans

| Sample | Standard Level |
| --- | --- |
| A Day 18 | 100,000 |
| A Preimm. | 1,886 |
| A Preimm. | 2,349 |
| B | 1,600 |
| C | 1,742 |
| D | 1,839 |
| D | 1,769 |
| E | 1,481 |
| F | 1,781 |
| G | 2,145 |
| H | 2,600 |
| I | 1,397 |
| J | 1,390 |
| K | 1,798 |
| L | 1,539 |

$\frac{100,000}{1,808}$ = 55-fold increase    x = 1,808

In 18 days after 1 injection = 352
of 1.0 mg
6 μg/lb body weight

No systemic toxic effects. Only local soreness and redness.

EXAMPLE X

Protection of Infants Against Coli bacillosis neonatorum

Pregnant mothers are inocculated with the *E. Coli* pilus vaccine as set forth above, suitably 60 and preferably again 30 days prepartum. The newborn infant is protected either by being suckled by the mother immediately postpartum or the mother's colostrum is withdrawn and fed to the infant. It should be noted that the antibodies are present in the colostrum, thus protection may be provided to the newborn of others by a Lactating immunized mother.

I claim:

1. A method of protecting human subjects against colibacillosis caused by a member of a predetermined first group of strains of piliated *E. coli* which comprises administering to a subject in need of protection a composition capable of raising the antibody level of a human subject to a level sufficient to provide protection against infection caused by a member of a first group of strains of piliated *E.coli* comprising pili previously separated from other *E.coli* organism components derived from at least one member selected from a second group consisting of strains of piliated *E. coli* organisms having Type 1 pili and those having NMS pili wherein cells of organisms of said first group are agglutinable by serum containing antibodies against pili from said second group, said first group consisting of strains which may be the same as or different from the strains of said group.

2. A method of claim 1 wherein the vaccine composition is administered at least once to the subjects between about 5 and about 60 days before infection.

3. A method of claim 2 wherein there is administered between 1 and 100 μg/Kg body weight of the pilic component of vaccine composition.

4. A method of claim 1 wherein the pilic component of the vaccine composition is derived from Type 1 pili or NMS pili of *E. coli* H 10407 (ATCC 31705) or *E. coli* E-25 (ATCC 31703).

* * * * *